United States Patent [19]

Ammann et al.

[11] 4,265,280

[45] May 5, 1981

[54] CONNECTOR MEMBER FOR SEALED CONDUITS

[75] Inventors: David W. Ammann, Boulder, Colo.; Daniel B. Granzow, Ingleside, Ill.

[73] Assignee: Baxter Travenol Laboratories, Inc., Deerfield, Ill.

[21] Appl. No.: 5,749

[22] Filed: Jan. 23, 1979

[51] Int. Cl.³ .............................................. B65B 3/04
[52] U.S. Cl. .................................... 141/98; 141/382; 156/272; 285/3; 285/67
[58] Field of Search .................... 222/541; 141/1, 392, 141/98, 114, 311 R, 382-388; 250/338; 285/3, 4, 67, 325; 156/272, 289, 250, 251, 252, 253, 261, 306; 219/221 LK, 221 LL

[56] References Cited

U.S. PATENT DOCUMENTS

| 79,343 | 6/1868 | Hamilton | 285/67 |
|---|---|---|---|
| 331,998 | 12/1885 | Parsels | 285/67 |
| 3,083,916 | 4/1963 | Neel | 222/541 |
| 3,169,562 | 2/1965 | Gogel | 222/541 |
| 3,364,930 | 1/1968 | Ryan | 222/541 |
| 3,491,752 | 1/1970 | Cowley | 222/541 |
| 3,764,796 | 10/1973 | Gilliam et al. | 222/541 |
| 3,964,643 | 6/1976 | Morane et al. | 222/541 |
| 4,122,980 | 10/1978 | Laverty | 222/541 |
| 4,157,723 | 6/1979 | Granzow | 141/1 |

Primary Examiner—Houston S. Bell, Jr.
Attorney, Agent, or Firm—Paul C. Flattery; Garrettson Ellis

[57] ABSTRACT

An improved connector member is provided for providing sealed and preferably sterile connection between a pair of conduits which each terminate in a hollow, transparent housing where some of the wall portion of each housing comprises an opaque wall portion sealed to the remainder of the housing. The opaque wall portions of each housing are positioned in facing contact with each other and are held in sealed, retentive relationship so that exposure to radiant energy causes them to fuse and open an aperture therethrough. In accordance with this invention, improved retention means are provided to permit the respective housings to be moved together in a path which is generally parallel to the opaque walls into sliding retaining relation. Also, the conduit communicating with the housings may be internally sealed, being openable from the exterior.

17 Claims, 11 Drawing Figures

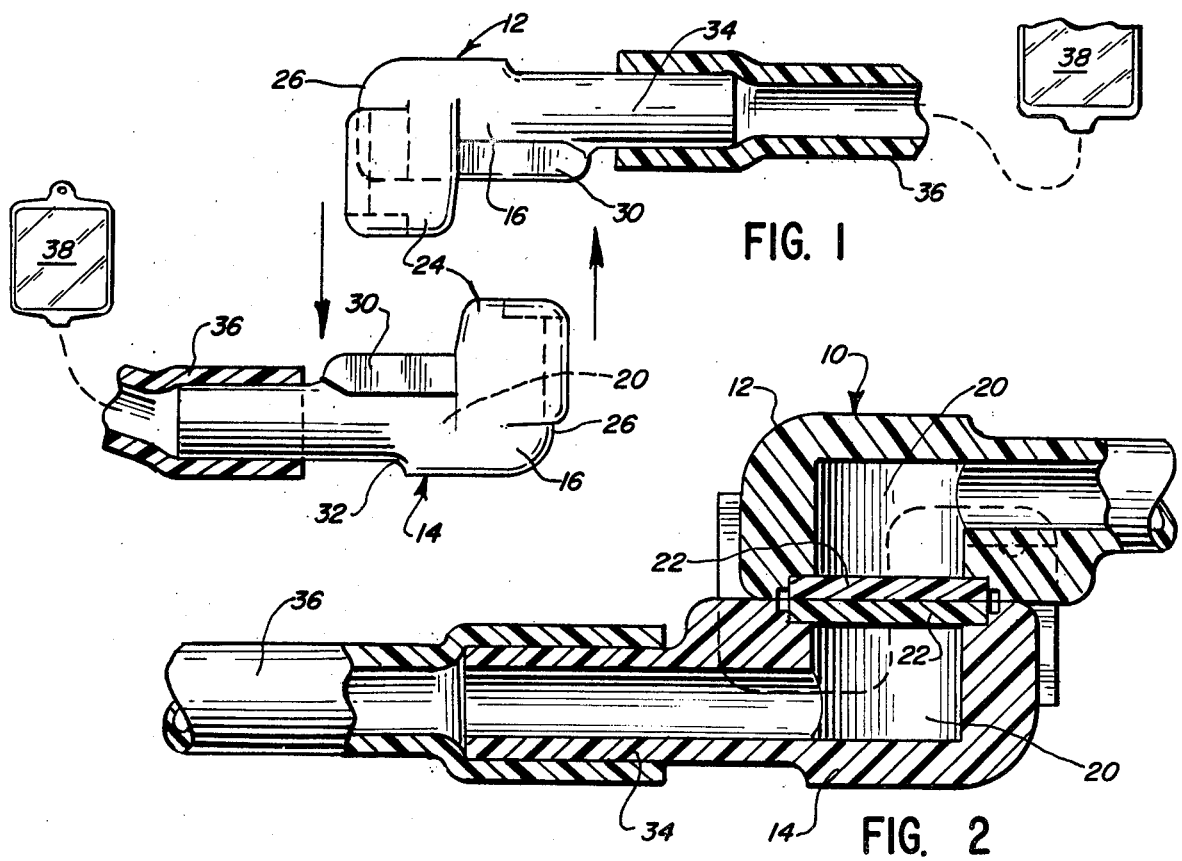
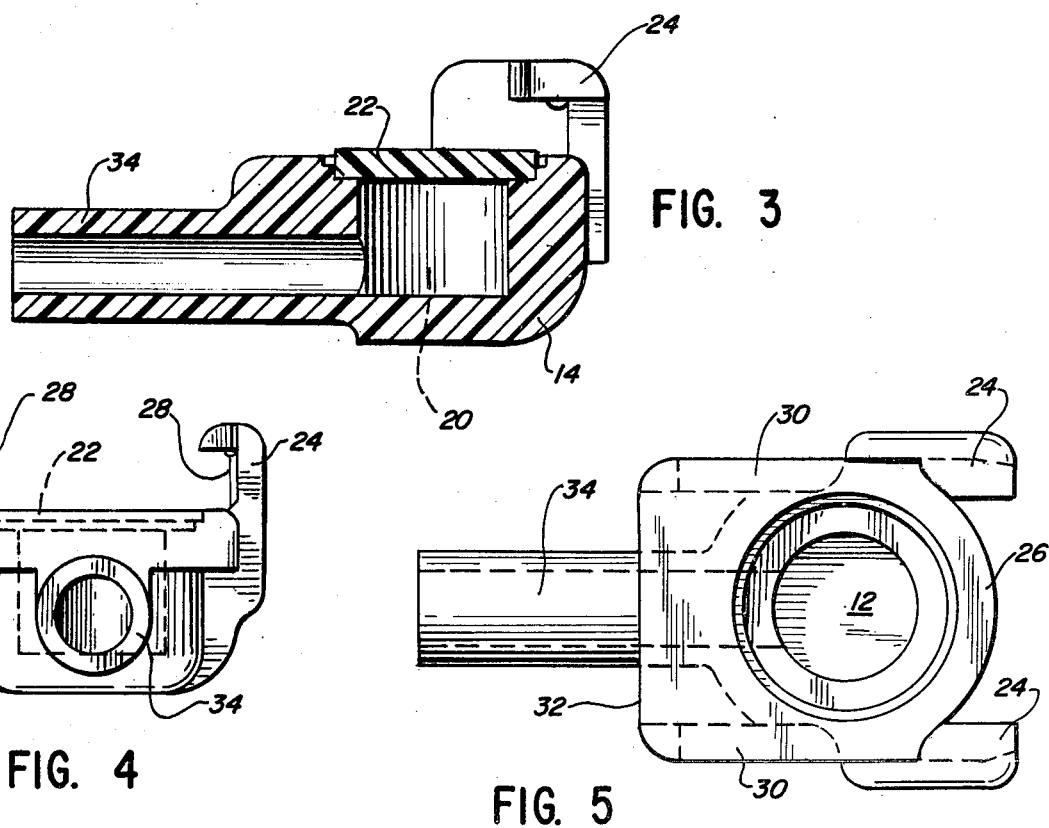

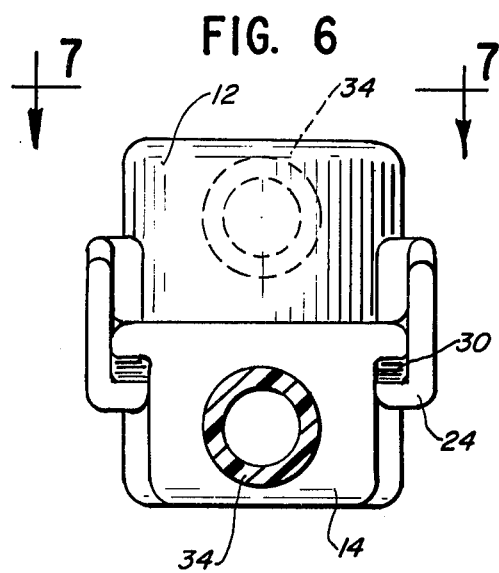
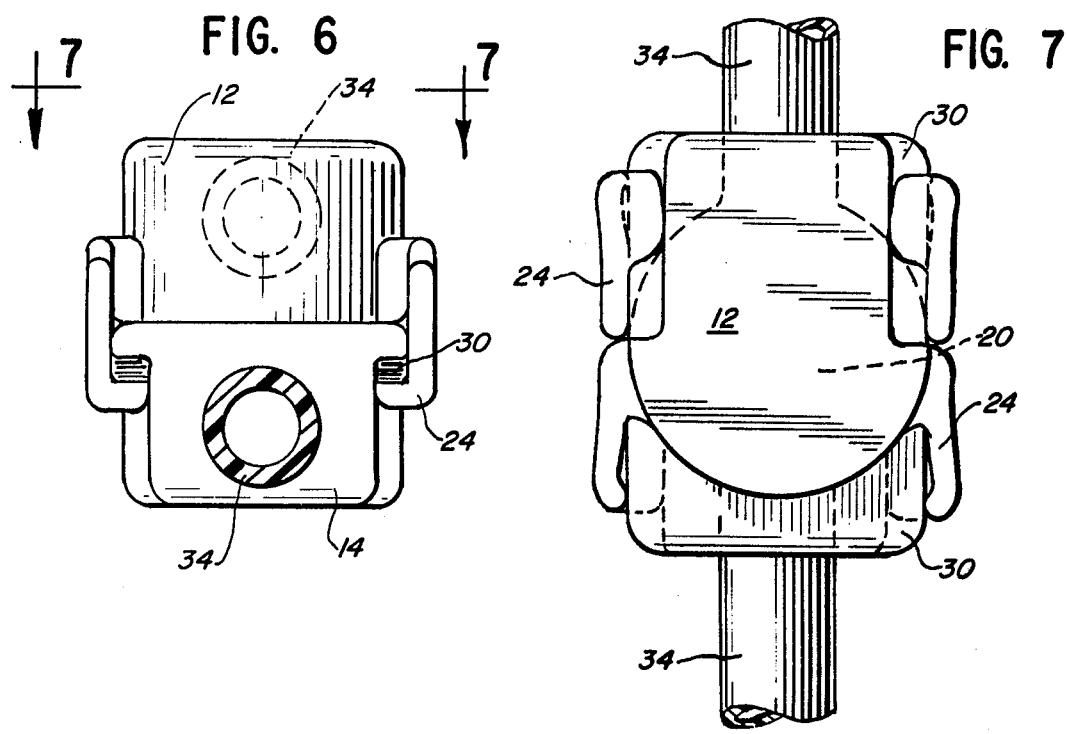
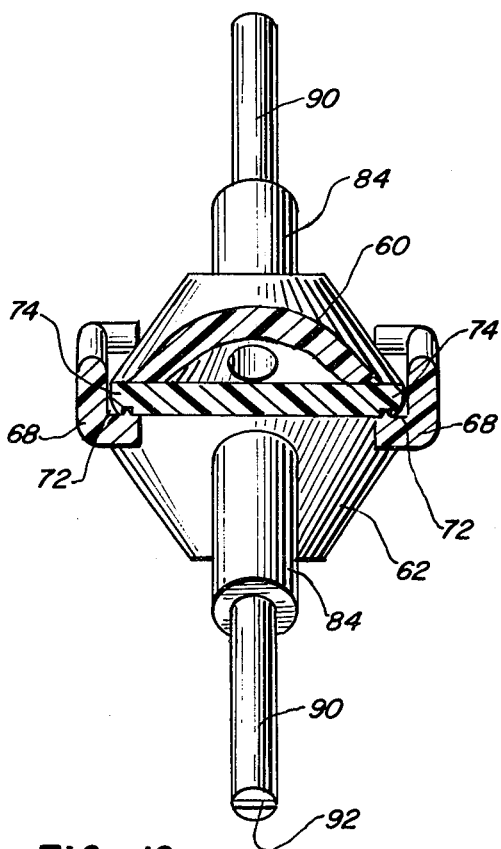
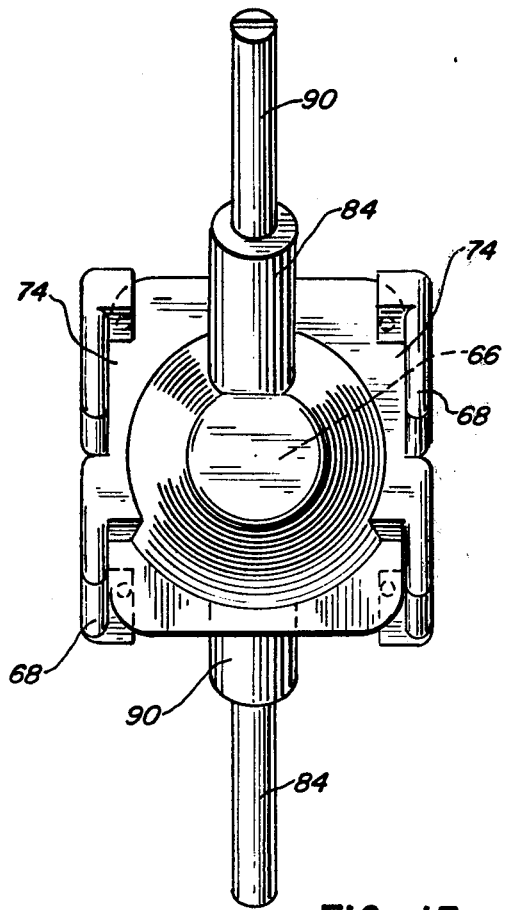
FIG. 6
FIG. 7
FIG. 12
FIG. 13

CONNECTOR MEMBER FOR SEALED CONDUITS

BACKGROUND OF THE INVENTION

In U.S. Patent Application Ser. No. 843,608, filed Oct. 19, 1977 by Daniel B. Granzow, et al., now U.S. Pat. No. 4,157,723, member is shown for providing preferably sterile connection between the ends of conduits, for example, conduits which communicate with blood bags. Accordingly, when sealed, sterile connection is guaranteed, portions of blood, blood components, or other medical materials, for example, can be removed from one container and placed in another in sterile manner, after the connection has been made and a sealed connection provided by exposure to radiant energy as described in the previously cited application.

This present application relates to improvements in the design of the connector member, for added convenience and reliability of manufacture and use.

DESCRIPTION OF THE INVENTION

In accordance with this invention, a connector member providing sealed connection comprises a pair of connector elements which, in turn, each include a pair of hollow, transparent housings. The hollow interiors of each of the housings are sealable from the exterior, with some of the wall of each housing comprising an opaque wall portion separating the hollow housing interior from the exterior. Each opaque wall portion is sealed to the remainder of the transparent housing, said housings being positioned together with the opaque wall portions in facing contact with each other and held in sealed, retentive relationship. Accordingly, upon exposure of the connected housings to radiant energy, the opaque wall portions in facing contact can fuse together to open an aperture therethrough.

In accordance with this invention, retention means are carried by the connector elements of the connector member for retaining the housings together. The retention means include track-defining gripper arm means positioned adjacent the first end of each housing, and flange means positioned adjacent a second end of the housing. The flange means of each housing are adapted to fit in sliding, retaining relation within the track defined by the gripper arms means of the other housing, to retain the housing together in the sealed retentive relation with the opaque wall portions in facing contact. The flange means and the tracks defined by the gripper arm means occupy a plane which is parallel to the facing opaque wall portions.

Preferably, the track-defining gripper arm means comprises an opposed pair of gripper arms positioned on one side of each connector element. Similarly, the flange means preferably comprises an opposed pair of straight flanges positioned and proportioned to be received by the gripper arms of the other connector elements.

Also, each connector element has a conduit member which communicates with the hollow interior of the housing. The conduit member in turn may be positioned in sealed relation within the bore of the flexible tubing which may communicate with a blood bag or the like so that each connector element provides a sealed end to the flexible tubing.

The outer end of the conduit member, generally positioned within the bore of the flexible tubing, preferably defines a closed end wall with a projecting member extending outwardly from the closed end wall. Accordingly, manual bending of the projecting member can cause the rupture of the end wall to permit the opening of the outer end of the conduit member.

Referring to the drawings,

FIG. 1 is an elevational view of a pair of connector elements prior to being positioned together into a sealed connector member.

FIG. 2 is a partial vertical sectional view of the connector member made from the separate connector elements of FIG. 1.

FIG. 3 is a longitudinal sectional view of a connector element of FIG. 2.

FIG. 4 is an end elevational view of a connector element of FIG. 1.

FIG. 5 is a top plan view of a connector element of FIG. 1.

FIG. 6 is an end elevational view of the connector member of FIG. 2.

FIG. 7 is a plan view of the connector element of FIG. 2.

FIG. 12 is an elevational view, with parts broken away, of the joined connector elements of FIG. 10.

FIG. 13 is a plan view of the joined connector elements of FIG. 10.

Figure 9:
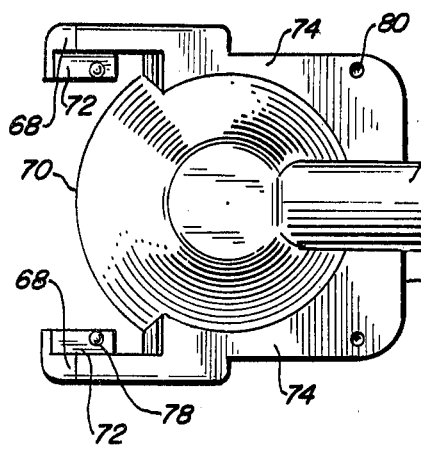
FIG. 9 is a top plan view of the connector element of FIG. 8.
Figure 8:
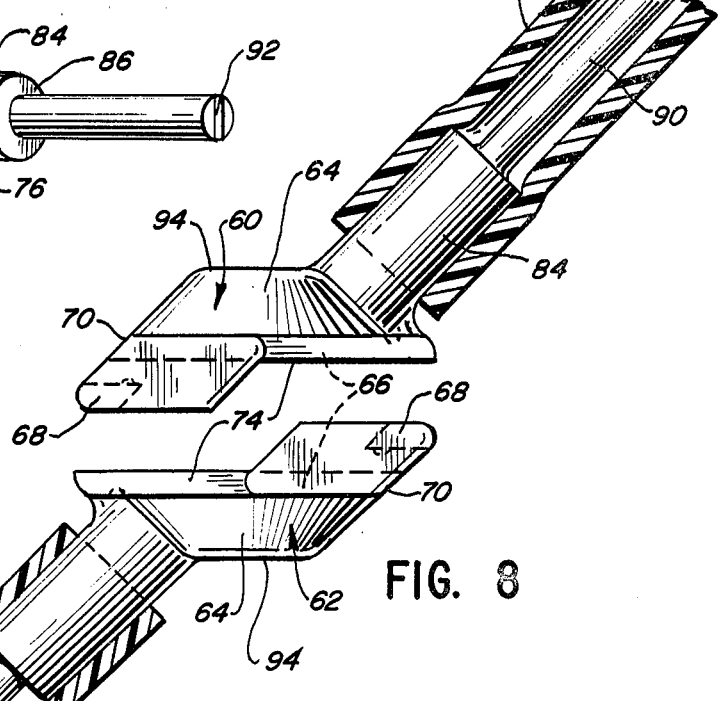
FIG. 8 is an elevational view, taken partly in section, of a pair of connector elements of a different embodiment of this invention, prior to being joined together into a sealed connector member.

Referring to FIGS. 1 through 5, a first embodiment of a connector member 10 which is made of its component connector elements 12, 14, is shown. Each of the pair of connector elements 12, 14 comprises a hollow, transparent housing 16 with the hollow interior 20 of each housing being sealable from the exterior.

A portion of the wall of each housing comprises an opaque wall portion 22 separating the hollow housing interior 20 from the exterior. Each opaque wall portion is sealed to the remainder of its transparent housing about the periphery of the wall portion 22.

Each housing 16 of the connector elements 12, 14 are adapted to be positioned together with the housing of the corresponding connector element, with the opaque wall portions 22 being positioned in facing contact with each other as shown in FIG. 2, and held in sealed, retentive relationship. Accordingly, upon exposure of the connected housing to radiant energy, in the manner described in the previously cited U.S. application Ser. No. 843,608, filed Oct. 19, 1977, now U.S. Pat. No. 4,157,723, the opaque wall portions in facing contact can fuse together and open an aperture therethrough.

Opaque wall portions 22 may preferably be made of an organic thermoplastic material, preferably one with a high melting or softening temperature, so that any bacteria residing upon the exterior surfaces of the opaque wall portions are killed by exposure to the melting or softening temperature of the opaque wall portion, as well as being entrapped in the melted mass. Specifically, the opaque wall portion 22 may be made of a polycarbonate material such as Lexan, sold by the General Electric Company, or various other preferably high-melting thermoplastic materials.

The thermoplastic opaque wall portion 22 generally contains a filler such as powdered charcoal, activated charcoal, or carbon black to render it opaque, although other desired fillers which are absorbant of the type of radiant energy to be used may be provided as a substitute for carbon.

Housings 16 are shown as being made of a transparent, high melting plastic material such as Lexan.

The radiant energy can be provided to the system by means of visible or incandescent, infrared, ultraviolet, or radio frequency energy as may be desired. The term "opaque" implies that the opaque wall portions are adapted to absorb a relatively high percentage of the particular radiant energy to which it is exposed. The term "transparent" implies that a lower percentage of the radiant energy applied is absorbed. Focused, infrared radiant energy is particularly desirable for use. Lasers may also be used as desired to provide the radiant energy.

Opaque wall portions 22 may be pre-stressed by uniaxial or biaxial orientation, or with radial stress patterns, to facilitate the formation of a central aperture as the opaque wall portions seal together. Also, unstressed wall portions may be used, with the central aperture formation taking place by cohesion during the heat-softening irradiation step.

Connector elements 14, 16 each carry means for retention to the other connector element. The retention means includes a pair of opposed gripper arm means 24 positioned adjacent a first end 26 of housing 16, and defining a track 28 for retaining a flange positioned within the track.

A pair of opposed flanges 30 are correspondingly positioned adjacent to a second end 32 of housing 16. Each of the flanges 30 and the tracks 28 defined by the gripper arms 24 are parallel to the opaque wall portion 22. The width of the tracks 28 is proportioned to be at least as great as the width of the flanges 30, so that the flanges 30 of the opposed connector element 12, 14 can fit into the tracks of gripper arm 24, and the flanges 30 of each connector element can fit into the tracks of the gripper arms 24 of the opposed connector element. Thus, the connector elements may be held together as a connector member in sealed relationship, as shown in FIG. 2, with opaque walls 22 in facing, abutting relation.

The respective connector elements are brought together by sliding together in a relative direction which is parallel to the plane of opaque walls 22. Accordingly, accidental forces which tend to pull the connector elements apart will not cause any separation at all, since the only possibility of relative motion is in the plane of tracks 28 and flanges 30.

Appropriate detent means may be provided to cause the connector elements 12, 14 to seal together into a snapfit relationship, to prevent the separation of the connector elements into separate components after they have been assembled.

After assembly, the connector elements may be irradiated by focused infrared radiation or the like for a desired period of time. For example, when a pair of opposed 150 watt Sylvania lamps of the eliptical reflector type (Model DJL) are used, the focused infrared light may be applied for about five seconds to effectively open an aperture through the pair of opaque walls 22, at the same time causing the opaque walls to fuse together about the aperture to provide a sealed flow path between the respective hollow interiors 20 of connector elements 12, 14. If desired, the lamp may be operated at less than 150 watts by use of a lower voltage, for reduction of the irradiation intensity.

Each connector element also defines a conduit member 34 which may be integrally molded with housing 16. In this embodiment, the conduit member 34 has an axis which is in longitudinal relationship to the plane of the attached opaque wall portion 22.

Preferably, conduit member 34 is positioned in sealed relation within the bore of flexible tubing 36 which, in turn, may communicate with a sealed container 38 such as a blood bag, a parenteral solution container, or the like. Accordingly, when the connector elements 12, 14 are brought together and irradiated, a sterile connection can open between two containers 38 for communication of fluids therebetween.

Referring to FIGS. 8 through 13, another embodiment of the connector of this invention is disclosed.

FIGS. 8 through 13 show a pair of connector elements 60, 62 which comprises, as before, a hollow, transparent housing 64 and an opaque wall 66 sealed at its periphery to the transparent housing 64 in a manner which is generally similar to the previous embodiment.

Retention means are carried by each connector element for retaining the housings 64 together. The retention means include opposed gripper arms 68 adjacent first end 70 of the housing which define a track 72, for receiving a flange 74, corresponding to flanges 30 in the previous embodiment, of the connector element to which connection is to be made.

Figure 10:
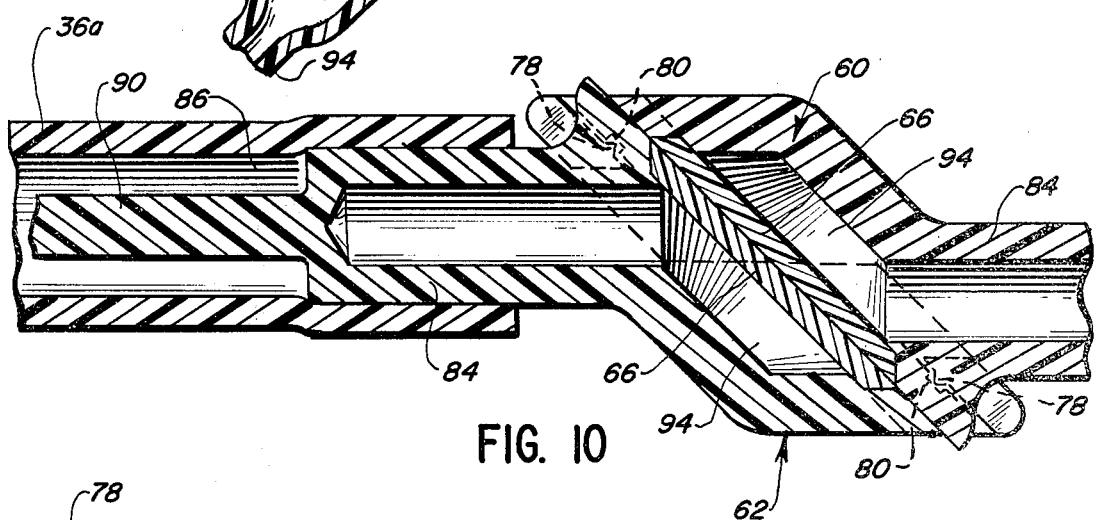
FIG. 10 is a fragmentary vertical sectional view of the connector member made from the joined connector elements of FIG. 8.
Figure 11:
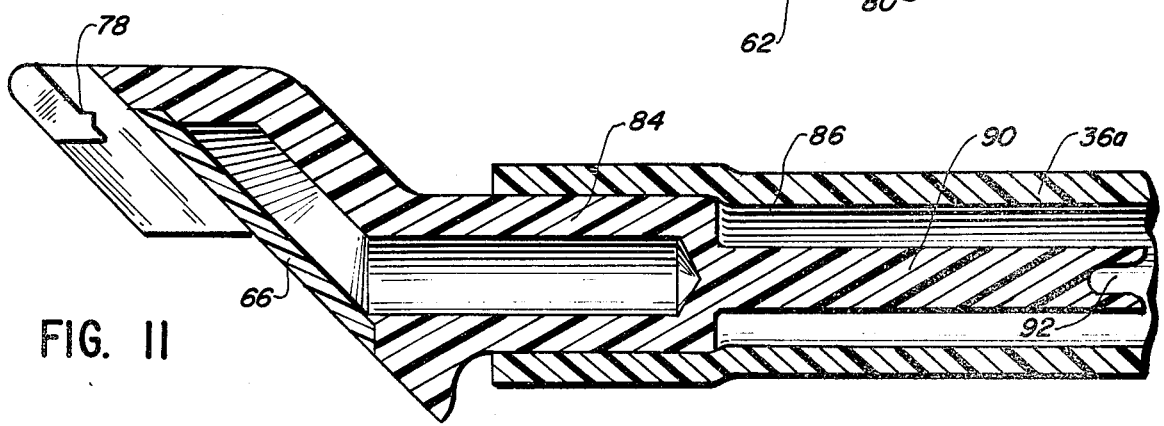
FIG. 11 is a longitudinal sectional view of a single connector member of FIG. 10.

In this embodiment, opposed flange members 74 are positioned adjacent to a second end 76 of each housing 64, the flanges 74 being adapted to fit in sliding, retaining relation with a track 72 defined by the gripper arm means of another connector element, for locking of the two connector elements together, with the opaque walls 66 in facing, abutting relationship as shown in FIG. 10.

Detent means 78, 80 are provided so that the respective connector elements 60, 62, after sliding into connecting, abutting relationship, are pulled apart again only with substantial difficulty in the common mode of use where, to insure sterility, the connector elements are intended to be permanently retained together after connection during their period of use.

Each connector element 60, 62 defines an integral conduit member 84, the axis of which, in this embodiment, defines an acute angle with the plane of its associated opaque wall portion 66. As shown herein, the outer end of the conduit member 84 defines a closed end wall 86, defining a thinned, frangible area (not shown) which may be annular in shape. A projecting member 90 extends outwardly from the closed end wall, so that manual bending of the projecting member 90 can cause rupture of the end wall 86 to permit the opening of the outer end of conduit member 84.

As in the previous embodiment, each conduit member 84 may be positioned in sealed relation within the bore of flexible tubing 36a, which may communicate with a sealed container 38, such as a blood bag. Accordingly, manual manipulation of the flexible tubing 36a and projecting member 90 permits the rupturing of end 86 of each conduit member 84, to open the connector elements 60, 62 after they have been connected together into a connector member as shown in FIG. 10.

When both of the connector elements carry the frangibly sealed ends 86 of their conduit member, it is often desirable to open one of them prior to the irradiation step. Then, air which is in the remaining sealed chamber 94 within housing 64 and conduit member 84 will expand during the heating step, providing a pressure differential across opaque walls 66 during the irradiation step. This in turn will assist in the rupturing of the opaque walls 66 as the walls weaken and melt, to provide a preferably sterile, sealed connection between the two connector elements 60, 62.

If desired, only one of the connector elements need to carry sealed end wall 86 and elongated member 90. For example, an empty blood bag might not utilize the sealed end wall 86 and elongated member 90, while a blood bag intended for receiving blood from a donor might carry the sealed end wall, to prevent traces of blood from passing upwardly to the opaque wall 66 during storage.

Elongated member 90 may terminate in a diametric slot 92. After breaking away, the slotted end of elongated member 92 may be pressed into constricted portion 94 of tubing 36a, to hold member 92 away from broken and open end 86. This prevents occluding of the flow passage. In this instance slot 92 permits flow through constricted portion 94 while member 92 is held therein.

The above has been offered for illustrative purposes only, and is not intended to limit the invention of this application, which is as defined in the claims below.

That which is claimed is:

1. In a connector member providing sealed connection, said connector member comprising a pair of hollow, transparent housings, the hollow interiors of each of said housings being sealable from the exterior, some of the wall of each housing comprising an opaque wall portion separating the hollow housing interior from the exterior, each opaque wall portion being sealed to the remainder of its transparent housing, said housings being positioned together with the opaque wall portions in facing contact with each other, and held in sealed, retentive relationship, whereby upon exposure of connected housings to radiant energy, the opaque wall portions in facing contact can fuse together and open an aperture therethrough, the improvement comprising:
retention means carried by said connector member for retaining said housings together, said retention means including: track-defining gripper arm means positioned adjacent a first end of each housing, and flange means positioned adjacent a second end of each housing, said flange means of each housing being adapted to fit in sliding retaining relation within the track defined by said gripper arm means of the other housing to retain said housings together in said sealed, retentive relation with the opaque wall portions in facing contact, said flange means and the tracks defined by the gripper arm means occupying a plane which is parallel to the plane of said facing, opaque wall portions.

2. A connector element for providing sealed connection with a second connector element of similar design, said connector element comprising a hollow, transparent housing communicating with a conduit member, the hollow interior of said housing being sealable from the exterior, some of the wall of said housing comprising an opaque wall portion separating the hollow housing interior from the exterior and sealable by connection to said second connector element with said opaque wall portion in facing contact with a corresponding opaque wall portion of the second connector element, and openable through said connector elements upon exposure of said opaque wall portions to radiant energy, thereby forming an edge-sealed aperture through said opaque portions and providing a virtually sterile connection through the joined connectors, and the improvement comprising: retention means carried by said connector element for retention to the second connector element, said retention means including: track-defining gripper arm means positioned adjacent a first end of said housing, and flange means positioned adjacent the second end of said housing, said flange means and the tracks defined by the gripper arm means being parallel to the opaque wall portion, the width of each track defined by the gripper arm means being at least as great as the width of said flange means, whereby the flange means may slideably fit into the corresponding gripper arm means of the second connector element, and the gripper arm means may receive corresponding flange means of the second connector element for sealing of the two connector elements into a single connector member with the opaque wall portions in facing contact.

3. The connector element of claim 2 in which said track-defining gripper arm means comprises an opposed pair of track-defining gripper arms.

4. The connector element of claim 3 in which said flange means comprises an opposed pair of straight flange edges.

5. The connector element of claim 4 in which a conduit member communicates with the hollow interior of said housing, said conduit member having an axis which is in longitudinal relationship to the plane of said opaque wall portions.

6. The connector element of claim 4 in which a conduit member communicates with the hollow interior of said housing, the axis of said conduit member defining an acute angle with the plane of the opaque wall portion.

7. The connector element of claim 6 in which the outer end of said conduit member defines a frangible closed end wall, a projecting member extending outwardly from said closed end wall, whereby manual bending of said projecting member can cause the rupture of said end wall to permit the opening of the outer end of said conduit member.

8. The connector element of claim 7 in which at least a portion of said conduit member is positioned in sealed relation within the bore of flexible tubing, said flexible tubing also enclosing the projecting member, whereby manipulation of the flexible tubing permits the rupturing of said closed end wall.

9. A connector element for providing sealed, sterile connection with a second connector element of similar design, said connector element comprising a hollow, transparent housing, the hollow interior of said housing being sealable from the exterior, a flat section of said housing wall comprising an opaque wall portion separating the hollow housing interior from the exterior and being sealable by connection to said second connector element in facing contact with a corresponding opaque wall portion of the second connector element, and openable through said connector elements upon exposure to of said opaque wall portions to radiant energy, thereby forming an edge-sealed aperture through said opaque portions and providing a virtually sterile connection through said connector, the improvement comprising: retention means as part of said connector element for retention to the second connector elements, said retention means including track-defining gripper arm means positioned adjacent the first end of the housing, and flange means positioned adjacent the second end of said housing, said flange means and the track defined by the gripper arm means occupying a plane which is parallel to the plane of said opaque wall portion, the width of the track defined by the gripper arm means being at least as great as the width of said flange means, whereby the flange means may slideably fit into the corresponding gripper arm means of the second connector element, and the gripper arm means may slideably receive corresponding flange means of the second connector element, for sealing of the two connector elements into a single connector member with the opaque wall portion in facing contact; a conduit member communicating with the hollow interior of said housing, the outer end of said conduit member defining a frangible closed end wall, and a projecting member extending outwardly from said closed end wall, and an annular area of weakness in said end wall about said projecting member, whereby manual bending of said projecting member can cause the rupture of said end wall to permit the opening of the outer end of said conduit member.

10. The connector element of claim 9 in which at least a portion of said conduit member is positioned in sealed relation within the bore of flexible tubing, said flexible tubing also enclosing the projecting member, whereby manipulation of the flexible tubing and projecting member permits the rupturing of said closed end wall.

11. A connector member made of a pair of the connector elements of claim 10 connected together with their respective opaque wall portions in facing contact.

12. A connector element for providing sealing sterile connection with a second connector element, said connector element comprising a hollow, transparent, housing the hollow interior of said housing being sealable from the exterior, a flat section of said housing wall comprising an opaque wall portion separating the hollow housing interior from the exterior and being sealable by connection to the said second connector element in facing contact with a corresponding opaque wall portion of the second connector element, and openable through said connector elements upon exposure of said opaque wall portions to radiant energy, thereby forming an edge-sealed aperture through said opaque portions and providing a virtually sterile connection through said connector, the improvement comprising a conduit member communicating with the hollow interior of said housing, the outer end of said conduit member defining a frangible closed end wall, and a projecting member extending outwardly from said closed end wall, whereby manual bending of said projecting member can cause the rupture of said end wall to permit the opening of the outer end of said conduit member.

13. The connector element of claim 12 in which at least a portion of said conduit member is positioned in sealed relation within the bore of flexible tubing, said flexible tubing also enclosing the projecting member, whereby manipulation of the flexible tubing permits rupturing of said outer wall.

14. The connector element of claim 13, in connection with a second connector element comprising a hollow sealed, transparent housing, and also having a flat section comprising an opaque wall portion separating the hollow housing interior of the second connector element from the exterior, said connector element being connected together with the respective opaque walls in facing contact.

15. The connector element of claim 12 in which the interior of said hollow transparent housing is sterile, said connector element being capable of providing sterile connection with a second connector element of similar design.

16. The connector element of claim 15 in which the axis of said conduit member defines an acute angle with the plane of said opaque wall portion.

17. The connector element of claim 1 in which the interior of said hollow transparent housing is sterile, said connector element being capable of providing sterile connection with a second connector element of similar design.

* * * * *

UNITED STATES PATENT AND TRADEMARK OFFICE
CERTIFICATE OF CORRECTION

PATENT NO. : 4,265,280
DATED : May 5, 1981
INVENTOR(S) : David W. Ammann et al.

It is certified that error appears in the above-identified patent and that said Letters Patent is hereby corrected as shown below:

Column 1, line 7, before "member" insert -- a connector --.

Column 7, line 2, "elements" should read -- element --.

Signed and Sealed this

Eighteenth Day of January 1983

[SEAL]

Attest:

GERALD J. MOSSINGHOFF

Attesting Officer     Commissioner of Patents and Trademarks